(12) United States Patent
Bess

(10) Patent No.: US 10,918,758 B1
(45) Date of Patent: Feb. 16, 2021

(54) MODULAR SELF-CONTAINED DOWNDRAFT VENTILATION SYSTEM TO MITIGATE CROSS CONTAMINATION OF AIRBORNE PATHOGENS

(71) Applicant: Gregory Jerome Bess, Hannibal, NY (US)

(72) Inventor: Gregory Jerome Bess, Hannibal, NY (US)

( * ) Notice: Subject to any disclaimer, the term of this patent is extended or adjusted under 35 U.S.C. 154(b) by 0 days.

(21) Appl. No.: 16/948,681

(22) Filed: Sep. 29, 2020

Related U.S. Application Data

(60) Provisional application No. 63/026,881, filed on May 19, 2020.

(51) Int. Cl.

| | |
|---|---|
| *F24F 3/16* | (2006.01) |
| *B01D 35/30* | (2006.01) |
| *A61L 9/20* | (2006.01) |
| *F24F 7/10* | (2006.01) |
| *F24F 13/04* | (2006.01) |
| *F24F 13/28* | (2006.01) |

(52) U.S. Cl.
CPC ................ *A61L 9/20* (2013.01); *B01D 35/30* (2013.01); *F24F 3/16* (2013.01); *F24F 3/161* (2013.01); *F24F 7/10* (2013.01); *F24F 13/04* (2013.01); *F24F 13/28* (2013.01); *A61L 2209/16* (2013.01); *F24F 2003/1667* (2013.01)

(58) Field of Classification Search
CPC .... F24F 3/16; F24F 13/04; F24F 13/28; F24F 3/161; B01D 35/30
See application file for complete search history.

(56) References Cited

U.S. PATENT DOCUMENTS

| | | |
|---|---|---|
| 3,107,974 A | 10/1963 | Potapenko |
| 3,511,162 A | 5/1970 | Truhan |
| 4,409,889 A | 10/1983 | Burleson |
| 4,667,580 A | 5/1987 | Wetzel |
| 4,693,173 A | 9/1987 | Saiki et al. |
| 4,838,150 A | 6/1989 | Suzuki et al. |
| 5,000,120 A | 3/1991 | Coiro, Sr. et al. |
| 6,910,497 B2 | 6/2005 | Bernard |
| 7,037,188 B2 | 5/2006 | Schmid et al. |
| 7,083,515 B2 | 8/2006 | Rapisarda et al. |
| 7,740,686 B2 | 6/2010 | Metteer |
| 8,132,535 B2 | 3/2012 | Correa et al. |
| 8,266,921 B2 | 9/2012 | Tashiro |
| 9,380,731 B2 | 6/2016 | Faig Palomer |
| 9,518,748 B2 | 12/2016 | Holtz et al. |

(Continued)

FOREIGN PATENT DOCUMENTS

JP        2009145338 A  *  7/2009  .............. F24F 3/161

*Primary Examiner* — Robert A Hopkins
(74) *Attorney, Agent, or Firm* — Dunlap Bennett & Ludwig, PLLC

(57) ABSTRACT

A modular self-contained downdraft ventilation system to mitigate cross contamination of airborne pathogens within an indoor environment. Low-pressure regions along the user supporting surface urges airflow through flooring collection modules that can be selectively interlinked to form the supporting surface. Ducting/transition modules fluidly interconnect the flooring collection modules and local air handler modules. The air handler modules provide radiation, ultraviolet light, and or filters for sterilizing the airflow prior to redistributing it back to the indoor environment.

10 Claims, 5 Drawing Sheets

(56) References Cited

U.S. PATENT DOCUMENTS

| | | |
|---|---|---|
| 10,492,970 B2 | 12/2019 | Merino et al. |
| 2007/0158499 A1 | 7/2007 | Whittingham |
| 2007/0202798 A1 | 8/2007 | Billiotte et al. |
| 2010/0003912 A1 | 1/2010 | Jeng et al. |

* cited by examiner

US 10,918,758 B1

MODULAR SELF-CONTAINED DOWNDRAFT VENTILATION SYSTEM TO MITIGATE CROSS CONTAMINATION OF AIRBORNE PATHOGENS

CROSS-REFERENCE TO RELATED APPLICATION

This application claims the benefit of priority of U.S. provisional application number 63/026,881, filed 19 May 2020, the contents of which are herein incorporated by reference.

BACKGROUND OF THE INVENTION

The present invention relates to indoor ventilation systems and, more particularly, a modular, deployable self-contained downdraft ventilation system to mitigate cross contamination of airborne pathogens.

The design of buildings that promote occupant health and well-being requires clear understanding of the ways that ventilation airflow interacts with, dilutes, and displaces pollutants within the occupied space. Although traditional ventilation is an integral component to maintaining good indoor air quality, it may not be satisfactory alone.

Current Heating, Ventilation, and Air Conditioning (HVAC) methodology allows and promotes cross contamination of airborne pathogens in an indoor environment through circulation of randomly moving airflow (the 'random air circulation problem'). In short, one infected person within the occupied space can rapidly infect multiple people in their immediate area and throughout the indoor environment with uncontrolled airflow due to the random air circulation problem.

As can be seen, there is a need for a modular, deployable self-contained downdraft ventilation system to mitigate cross contamination of airborne pathogens through airflow directed downdraft to counter the problem of random air circulation.

The present embodies a system that provides a positive, downdraft direction for ambient air to be channeled away from individuals and processed before being reintroduced or ejected from the area. This system creates a downward airflow effectively isolating individuals in their own airspace. Contaminated air is drawn downwards and channeled away to be sterilized and processed. The system can be rapidly configured to suit the space and end purpose without the need to alter existing building infrastructure.

SUMMARY OF THE INVENTION

In one aspect of the present invention, a ventilation system to mitigate cross contamination of airborne pathogens within an indoor environment, the system includes the following: one or more air handler modules having an inlet plenum fluidly coupled to an airflow urger; and a plurality of flooring collection modules defining a supporting surface, each flooring collection module having a plurality of airways fluidly connected to the inlet plenum, wherein the airflow urger is configured to induce a low-pressure region across the plurality of airways.

In another aspect of the present invention, the ventilation system to mitigate cross contamination of airborne pathogens within an indoor environment, the system includes the following: a plurality of air handler modules having an inlet plenum fluidly coupled to an airflow urger; one or more ducting modules that fluidly interconnect two adjacent air handler modules of the plurality of air handler modules; a plurality of flooring collection modules defining a supporting surface, each flooring collection module having a plurality of airways fluidly connected to the inlet plenum by way of one ducting module of the plurality of the one or more ducting modules, wherein the airflow urger is configured to induce a low-pressure region across the plurality of airways; a plurality of modular locks interconnecting the plurality of flooring collection modules; one or more perplex barriers disposed beneath the plurality of flooring collection modules and between the two adjacent air handler module; and at least one ultraviolet lamp disposed inside at least one of the plurality of air handler modules, the at least one ultraviolet lamp and at least one radiation element between the inlet plenum and the indoor environment, wherein at least one radiation element is configured to project an irradiation envelope outside of the air handler module.

These and other features, aspects and advantages of the present invention will become better understood with reference to the following drawings, description and claims.

DETAILED DESCRIPTION OF THE INVENTION

Itemized Parts List

11: is the air handler/sterilization kiosk module.
12: is the modular array.
12a: is the access module.
12b: is the collection module.
12c: is the ducting module transition module.
12d: is the access module.
14a: is the two-meter high Perspex barrier.
14b: is the one-meter high Perspex barrier.
16: is the module lock.
16a: is the post of lock 16.
16b: is the pin.
16c: is the tapered slot for lock pins 16b.
18: is the airflow.
20a: is the area of high intensity irradiation.

20b: is the area of continued irradiation envelopes exiting airflow.
22: are the UV 254 nm lamps.
24: are the LCD information screens.
25: is the hand sanitizing port.
26: is the high polish reflective venturi.
28: is the support equipment.
30: is the mixed flow blower.
40: is the Type 6MH central air filtration module.
42: is the perforated filter support.
44: are the radial flow HEPA canister filters.
46: is the outlet plenum.
48: is the inlet plenum.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a modular self-contained downdraft ventilation system to mitigate cross contamination of airborne pathogens within an indoor environment. Low-pressure regions along the user supporting surface urges airflow through flooring collection modules that can be selectively interlinked to form the supporting surface. Ducting/transition modules fluidly interconnect the flooring collection modules and local air handler modules for sterilizing the airflow prior to redistributing it back to the indoor environment.

Referring now to FIGS. 1 through 8, the present invention may include a modular downdraft ventilation system 10 adapted to mitigate cross-contamination of airborne pathogens through producing a low-pressure region by people's feet, along the supporting surface thereof. This in turn creates an induced airflow downward drawing contaminated air down and away from individuals, mitigating cross contamination which is otherwise exacerbated by conventional HVAC systems.

Figure 1:
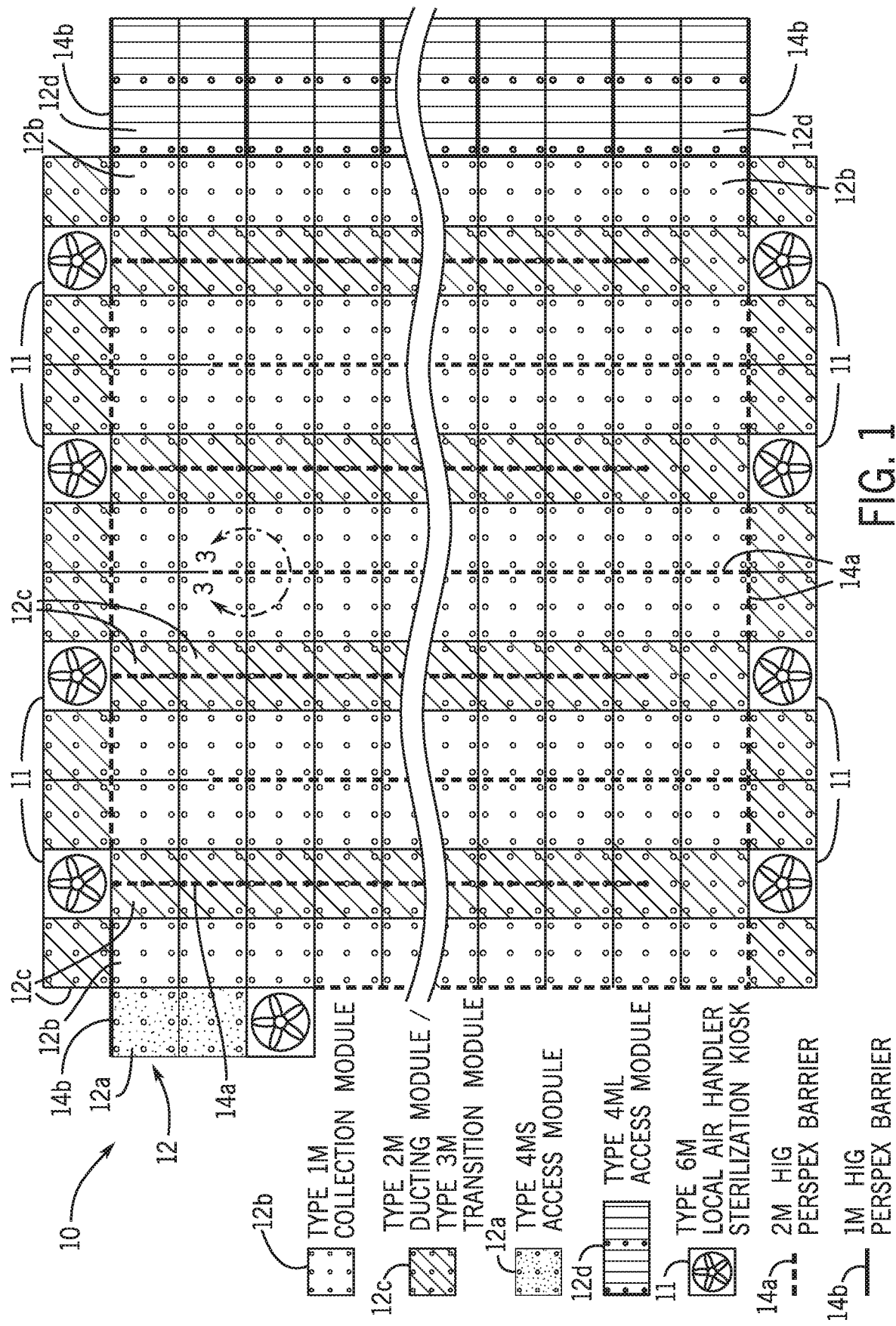
FIG. 1 is a schematic top plan view of an exemplary embodiment of a layout of the system embodied in the present invention.
Figure 2:
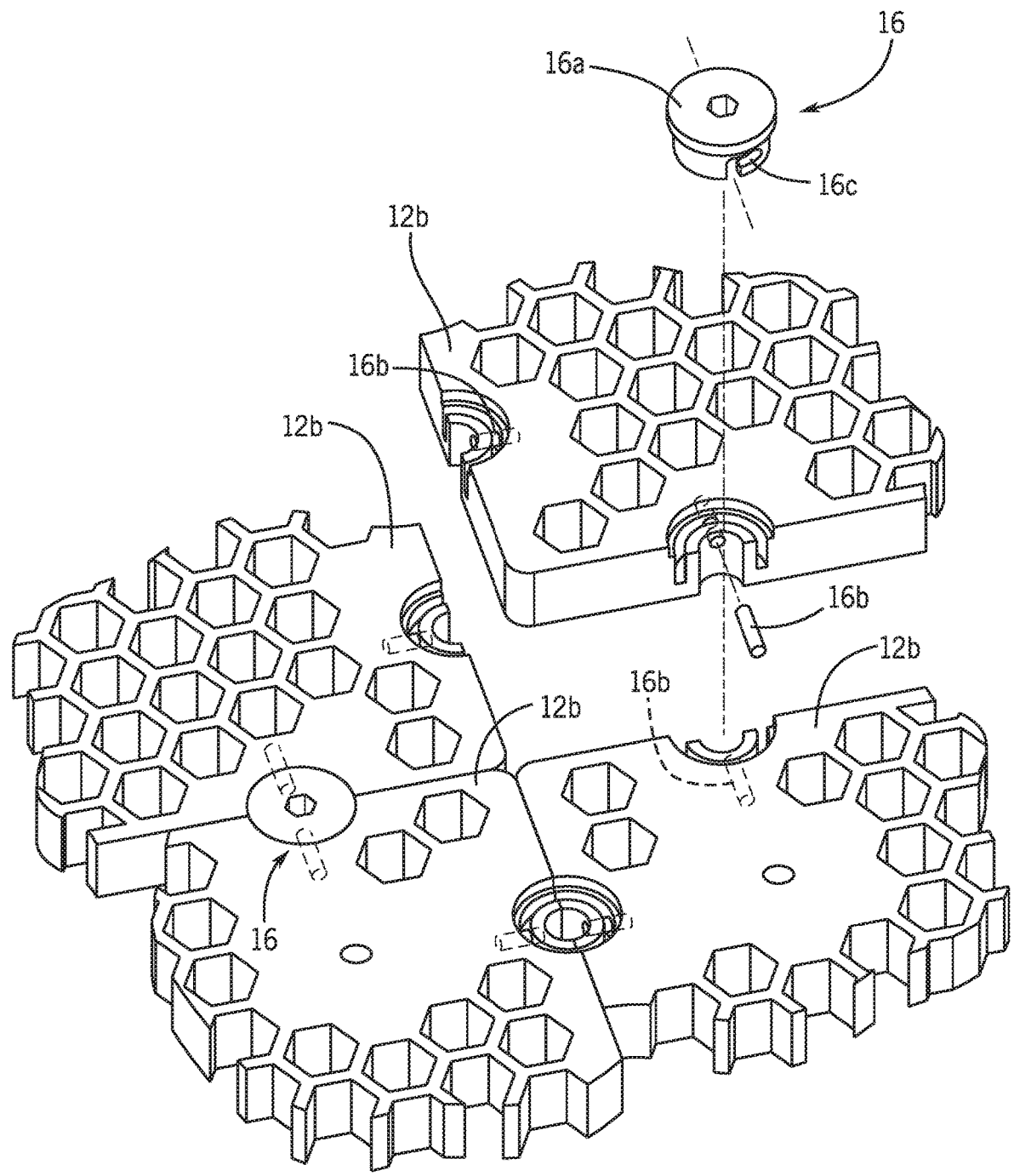
FIG. 2 is an exploded perspective view of an exemplary embodiment of flooring collection module of the present invention.
Figure 3:
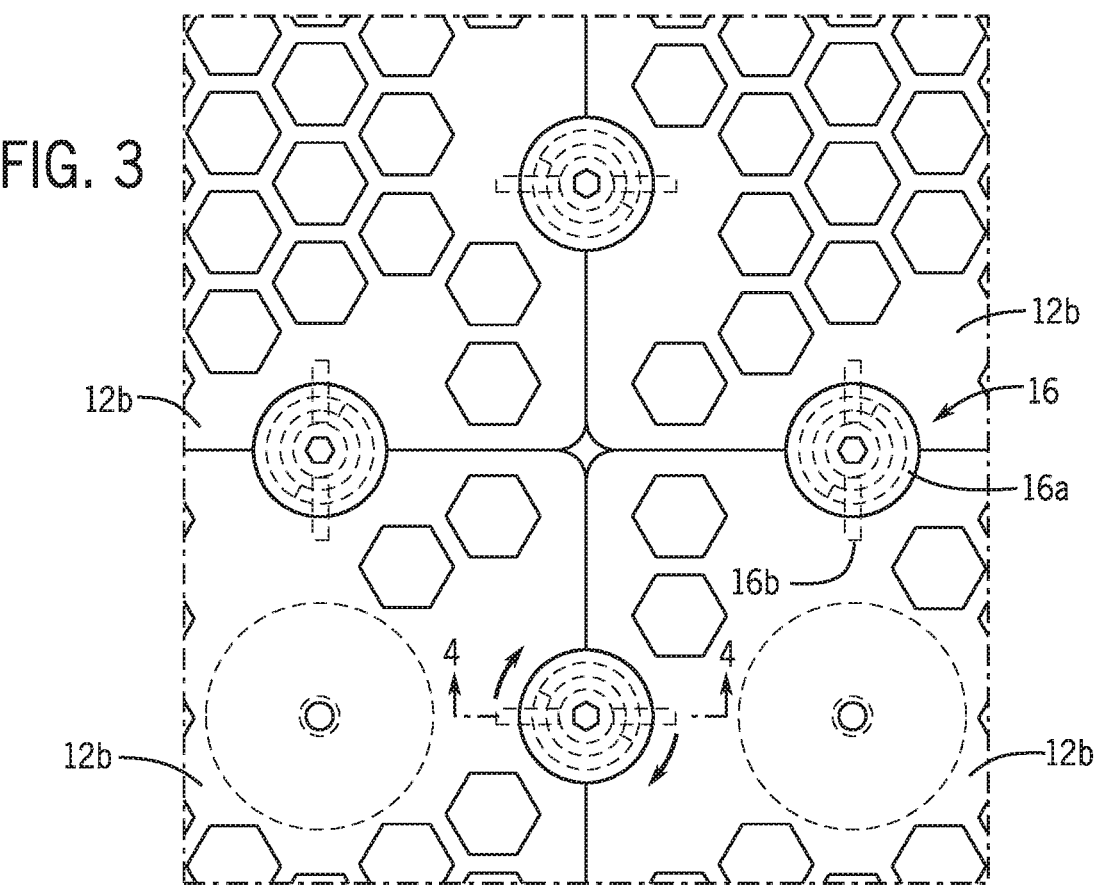
FIG. 3 is a top plan detail view of an exemplary embodiment of the present invention, indicated by the line 3-3 of FIG. 1.
Figure 4:
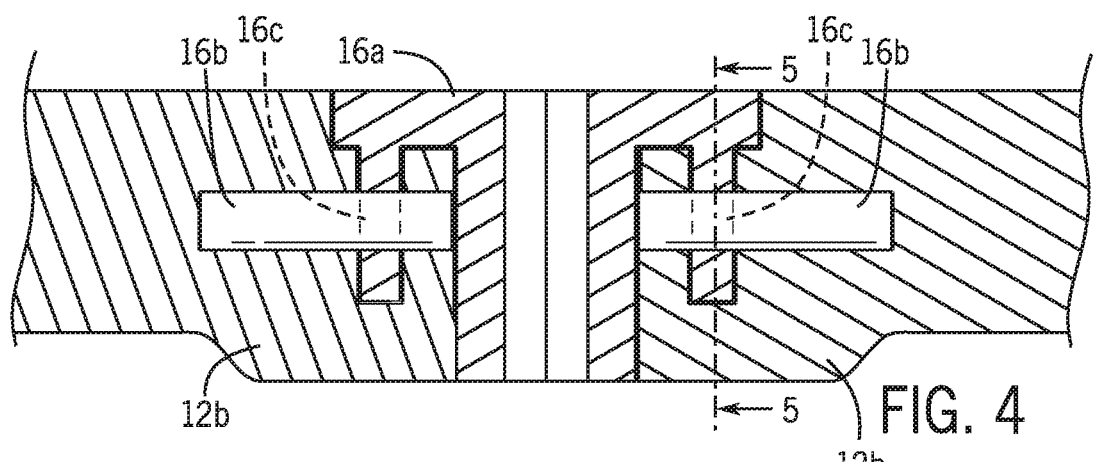
FIG. 4 is a cross-sectional view an exemplary embodiment of the present invention, taken on line 4-4 of FIG. 3.
Figure 5:
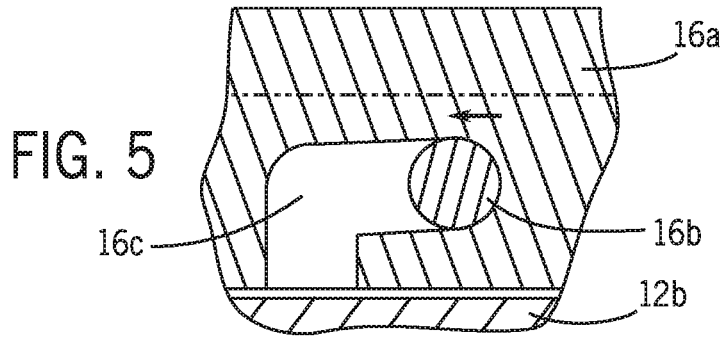
FIG. 5 is a cross-sectional view of an exemplary embodiment of the present invention, taken on line 5-5 of FIG. 4.
Figure 6:
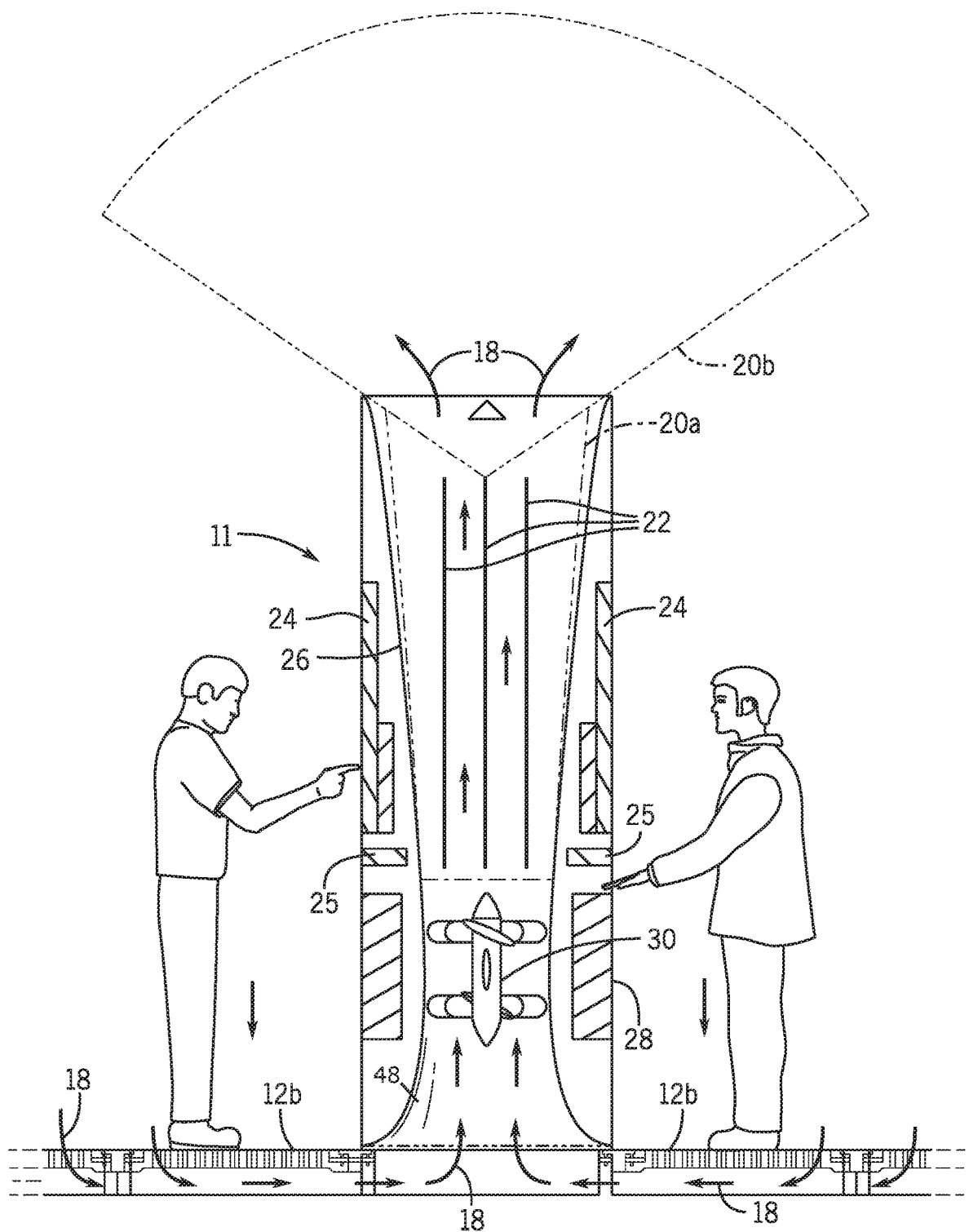
FIG. 6 is a side elevation view an exemplary embodiment of the present invention, showing a local air handler module 11 as a first ventilation kiosk in use.
Figure 7:
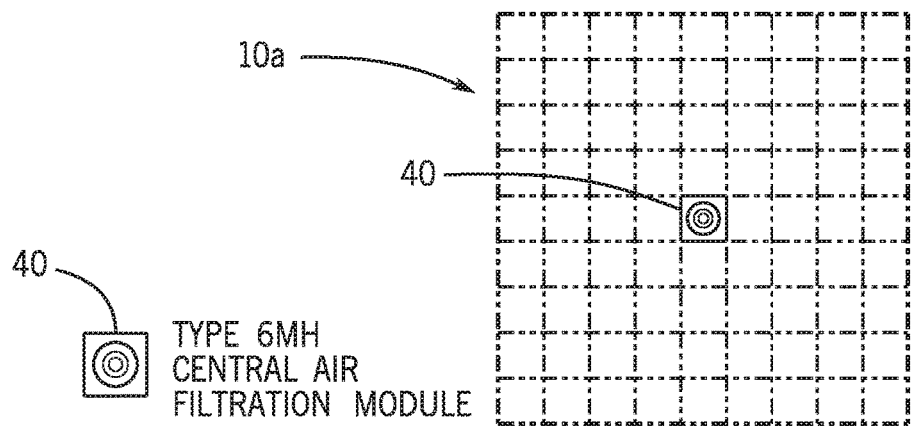
FIG. 7 is a schematic top plan view of an exemplary embodiment of an room-type indoor environment being serviced by the present invention.
Figure 8:
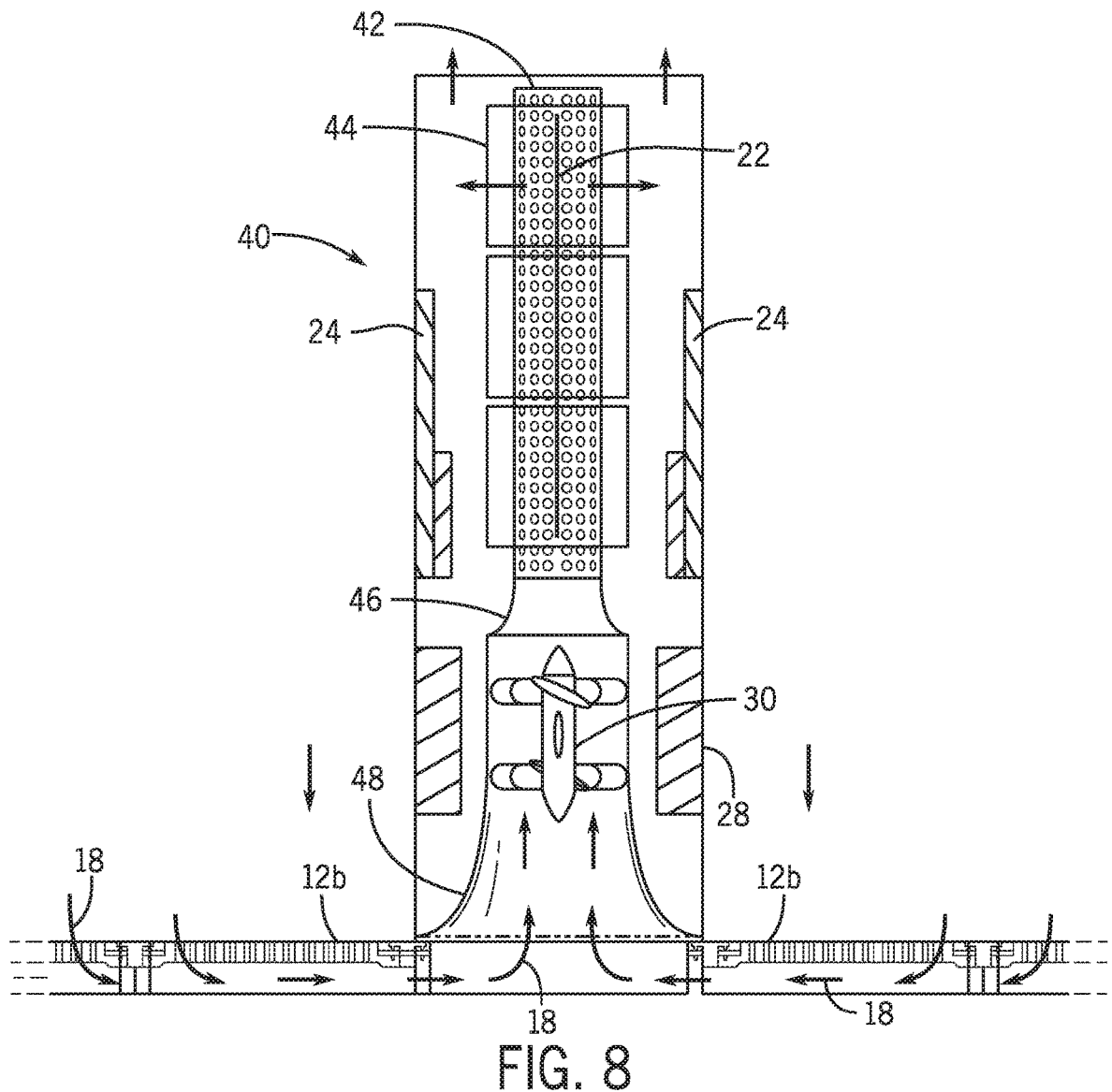
FIG. 8 is a side elevation view an exemplary embodiment of the present invention, showing a local air handler module 11 as a second ventilation kiosk (more adapted for smaller room type enclosures) in use.

FIG. 1 is the schematic room diagram of an exemplary embodiment of the modular downdraft ventilation system 10, which interchangeably and selectively includes the following modular systemic components:

(A) flooring collection modules 12b: may be the main component for system that provides a ventilated flooring platform. The flooring collection modules 12b may be referred to as Type 1M module.

(B) ducting module/transition modules 12c. The ducting module 12c is a solid top module that fluidly connects to flooring collection modules 12b to form duct-ways for air collected therefrom. The ducting module 12c may be referred to as a Type 2M module. The transition module 12c is also a solid top module that fluidly interconnects ducting module 12c (transitioning to) remote air handlers modules 11 via flexible ducting. The transition module 12d may be referred to as a Type 3M module.

(C) first access module 12a is solid top ramp module to access elevated flooring. The first access module 12a may be referred to as the Type 4MS module.

(D) second access module 12d is a low slope ramp module to access elevated flooring. The second access module 12d may be referred to as the Type 4ML module.

(E) local air handler modules 11 may include a sterilization kiosk module The sterilization kiosk module may be a freestanding self-contained system containing the following: (a) one or more high volume fans; (b) fan supports; (c) power supplies and telemetry; (d) a reflective venturi may be is made from spun aluminum and polished with conventional methods; (e) LCD screens for PSA's, advertising and instructions; (f) high-power UVGI lamps; (g) UVGI hand sanitizing ports; and/or (h) active noise reduction transducers. The local air handler modules 11 may be constructed with commercial off-the-shelf (COTS) electrical and electronic components eliminating excessive development curves. If desired, the local air handler modules 11 can be used remotely to remove and process contaminated air, processing the air locally and continuing to process the atmosphere in an enclosure even when unoccupied. The local air handler modules 12d may be referred to as a Type 6M or 6MH module.

(F) a first perspex barrier 14b and second Perspex barriers 14a, are transparent barrier supports which may be constructed from extruded aluminum. The first and second Perspex barrier 14b and 14a may be referred to as one-meter high and two-meter high, respectively.

Overall, the ducting module/transition modules 12c interconnect the local air handler modules 11 and the flooring collecting modules 12b are fluidly connected to the ducting module/transition modules 12c with the aid, in certain embodiments, the perpex barriers 14a and 14b.

FIGS. 2-5 show detailed views of flooring collection modules 12b operatively associated with each other. The flooring collection modules 12b may be manufactured by injection or roto molding plastic, wherein the molds are simple in design allowing them to be produced in facilities lower levels of sophistication.

Each flooring collection modules 12b may include a plurality of airways 13 for allowing the downward airflow 18 urged (therethrough by low-pressure region along the flooring collection modules 12b) from the enclosure indoor environment to the ducting module/transition modules 12c, which in turn fluidly communicate to the local air handler modules 11.

Each flooring collection modules 12b may be selectively linked through the use of module locks 16. Each module lock 16 may include a post 16a, a pin 16b, a tapered slot 16c for each lock pin 16b.

Referring to FIGS. 5-8, each local air handler modules 11 may include one or more of the following: an area of high intensity irradiation 20a, an area of continued irradiation envelopes exiting airflow 20b, UV 254 nm lamps 22, LCD information screens 24, hand sanitizing port 25, high polish reflective venturi 26, support equipment 28, mixed flow blower 30, a central air filtration module 40, a perforated filter support 42, radial flow HEPA canister filters 44, an outlet plenum 46 and an inlet plenum 48.

When the modular downdraft ventilation system 10 is assembled it produces a low pressure region by people's feet, this in turn creates an induced airflow 18 downward drawing contaminated air down and away from individuals-through the flooring collection modules 12b, then through the ducting module/transition modules 12c, and reaching a local air handler module 11. At the local air handler module 11 inlet plenum receives the airflow 18 and treats the airflow to high intensity irradiation 20a, ultraviolet lights 22, filters 42.

A method of using the present invention may include the following. The modular downdraft ventilation system 10 disclosed above may be provided. To implement the design one assesses the size of the area to cover, the desired traffic pattern whether it be a serpentine line such as an airline check-in or security queue, a straight line such as a workstation or voting line or static with lower barriers such as a seated classroom, theatre or waiting area. The number and type of flooring collection modules 12b is calculated to cover the required area and barriers 14a and 14b are placed according to the required traffic pattern. The flooring collection modules 12b can easily be adapted to fit different length and width scenarios and irregularly shaped rooms. Finally, the number of air handlers are chosen and placed.

Additionally, the present invention can be adapted or re-configured for temporary medical treatment facilities where beds are used as well as manufacturing lines where overall effectiveness exceeds simple physical barriers.

It should be understood, of course, that the foregoing relates to exemplary embodiments of the invention and that modifications may be made without departing from the spirit and scope of the invention as set forth in the following claims.

What is claimed is:

1. A ventilation system to mitigate cross contamination of airborne pathogens within an indoor environment, the system comprising:
    one or more air handler modules having an inlet plenum fluidly coupled to an airflow urger; and
    a plurality of flooring collection modules defining a supporting surface, each flooring collection module having a plurality of airways fluidly connected to the inlet plenum, wherein the airflow urger is configured to induce a low-pressure region across the plurality of airways.

2. The ventilation system of claim 1, further comprising a plurality of modular locks interconnecting the plurality of flooring collection modules.

3. The ventilation system of claim 2, wherein each modular lock comprises two pins interconnecting adjacent flooring collection modules of the plurality of flooring collection modules, and wherein each modular lock comprises a post with two tapered slots for rotatably engaging the two pins.

4. The ventilation system of claim 1, further comprising one or more ducting modules that fluidly interconnect two adjacent air handler modules of the one or more air handler modules, wherein each flooring collection module fluidly connects to each ducting module.

5. The ventilation system of claim 4, further comprising one or more perplex barriers disposed beneath the plurality of flooring collection modules and between the two adjacent air handler modules.

6. The ventilation system of claim 1, further comprising at least one ultraviolet lamp disposed inside at least one of the one or more air handler modules, the at least one ultraviolet lamp between the inlet plenum and the indoor environment.

7. The ventilation system of claim 1, further comprising at least one radiation element disposed inside at least one of the one or more air handler modules, the radiation element between the inlet plenum and the indoor environment.

8. The ventilation system of claim 7, wherein at least one radiation element is configured to project an irradiation envelope outside of the air handler module.

9. A ventilation system to mitigate cross contamination of airborne pathogens within an indoor environment, the system comprising:
    a plurality of air handler modules having an inlet plenum fluidly coupled to an airflow urger;
    one or more ducting modules that fluidly interconnect two adjacent air handler modules of the plurality of air handler modules;
    a plurality of flooring collection modules defining a supporting surface, each flooring collection module having a plurality of airways fluidly connected to the inlet plenum by way of one ducting module of the plurality of the one or more ducting modules, wherein the airflow urger is configured to induce a low-pressure region across the plurality of airways;
    a plurality of modular locks interconnecting the plurality of flooring collection modules;
    one or more perplex barriers disposed beneath the plurality of flooring collection modules and between the two adjacent air handler module; and
    at least one ultraviolet lamp disposed inside at least one of the plurality of air handler modules, the at least one ultraviolet lamp and at least one radiation element between the inlet plenum and the indoor environment.

10. The ventilation system of claim 9, wherein at least one radiation element is configured to project an irradiation envelope outside of the air handler module.

* * * * *